United States Patent [19]
Kleinloh et al.

[11] Patent Number: 5,921,089
[45] Date of Patent: Jul. 13, 1999

[54] METHOD FOR THE TRANSPORT AND STORAGE OF PHENOL

[75] Inventors: Werner Kleinloh, Haltern, Germany; Otto Schnurr, Kapellen; Tony Van Osselaer, Belsele, both of Belgium; Claus Wulff, Krefeld; Gottfried Zaby, Leverkusen, both of Germany

[73] Assignees: Phenolchemie GmbH & Co. KG, Gladbeck; Bayer AG, Leverkusen, both of Germany

[21] Appl. No.: 08/942,613

[22] Filed: Oct. 2, 1997

[30] Foreign Application Priority Data

Oct. 2, 1996 [DE] Germany .............................. 196 40 710

[51] Int. Cl.$^6$ ........................................................ F17C 11/00
[52] U.S. Cl. ................................................ 62/46.1; 62/45.1
[58] Field of Search ........................................ 62/46.1, 45.1; 44/450

[56] References Cited

U.S. PATENT DOCUMENTS

| | | | |
|---|---|---|---|
| 4,375,567 | 3/1983 | Faler ........................................ | 568/727 |
| 4,480,134 | 10/1984 | Fulmer ..................................... | 568/385 |
| 4,567,304 | 1/1986 | Fulmer ..................................... | 568/385 |
| 5,300,700 | 4/1994 | Malamet et al. ........................ | 568/723 |

*Primary Examiner*—Christopher B. Kilner
*Attorney, Agent, or Firm*—Oblon, Spivak, McClelland, Maier & Neustadt, P.C.

[57] ABSTRACT

The transportation and storage of phenol is enhanced by additions of up to 70% by weight of acetone to liquid phenol.

11 Claims, No Drawings

METHOD FOR THE TRANSPORT AND STORAGE OF PHENOL

BACKGROUND OF THE INVENTION

Field of the Invention

Phenol is a base product of petrochemistry, of which more than 5 million metric tons are produced per year worldwide. Phenol serves as starting product for numerous intermediates and finished products. A large proportion of the phenol is further processed to form phenol-formaldehyde resins. In addition, bisphenol A (2,2'-di-(4-hydroxyphenyl)propane) is prepared from phenol and acetone to a great extent, since bisphenol A has become of increasing importance as a starting product for polycarbonates and epoxy resins.

Phenol has a melting or solidification point of 41° C.; it is therefore solid at the usual ambient temperatures. However, phenol is handled in solid form only in insignificantly small amounts. Phenol is customarily transported and stored as a liquid at temperatures above its solidification point. In order to keep the phenol liquid, the piping, transhipment facilities and the storage and transport vessels are customarily insulated against heat losses. An additional heating means is generally also required. Thermally insulated, treated transport and storage systems are therefore usually used.

The vessel material used is generally steel. Phenol has a tendency to discolor owing to oxidation products of phenol. If the phenol is to remain colorless for as long as possible, transport and storage systems made of stainless steel are used.

During the storage and transport of liquid phenol, care must be taken to keep the temperature below 70° C., since the lower explosive limit for phenol/air mixtures is reached at a saturation temperature of approximately 73° C. At storage temperatures above the flash point, the gas space in the vessel must be rendered inert by complex measures, e.g. by introducing nitrogen gas.

Another known commercial form of phenol is a mixture of phenol with water, in which case, by addition of water, in theory, a solidification point of the phenol/water mixture can be set between 0° C. and 41° C. However, in practice, only the concentration range of 8 to 10% by weight of water in the mixture is employed. If more water is added to the system, it divides into a water-rich and a phenol-rich phase. The phenol/water system has a miscibility gap (cf. Ullmanns Encyklopadie der technischen Chemie [Ullmanns Encylopaedia of Industrial Chemistry], 4th edition, 1979, vol. 18, p.177) below 69° C. A mixture of phenol with approximately 10% by weight of water has a solidification point of approximately 13.5° C.; a mixture with 20% by weight of water has a solidification point of approximately 5° C. The miscibility gap of the phenol/water system at 10° C. is between phenol contents of 7% by weight and 75% by weight. However, depending on climatic conditions, temperatures of 0° C. and below can also occur during transport and storage of phenol. Therefore, even the addition of water to the phenol does not avoid the need in every case for the use of treatable thermally insulated vessels. Furthermore, the water, depending on the phenol application must generally be removed from the phenol again later by complex means.

The object of the present invention is therefore to provide a method for the transport and storage of phenol in the liquid phase which does not require the use of treatable thermally insulated systems under conventional transport and storage conditions.

SUMMARY OF THE INVENTION

This object is achieved according to the invention by a method for the transport and storage of phenol as claimed in patent claim 1, which involves adding up to 70% by weight of acetone to the liquid phenol. Preferably, the acetone content in the phenol/acetone mixture is between 20 and 60% by weight, particularly preferably between 45 and 55% by weight. The mixtures thus obtained can be stored or transhipped and transported as liquid phase without additional heating and thermal insulation under appropriate climatic conditions.

DESCRIPTION OF THE PREFERRED EMBODIMENTS

The phenol/acetone system does not have a miscibility gap, and mixtures having solidification points below 0° C. may be readily established. A mixture of phenol with 15% by weight of acetone, for example, has a solidification point of approximately 20° C.; at 50% by weight of acetone a solidification point of approximately 0° C. is reached, and at 70% by weight of acetone, a solidification point of −40° C. is reached. Phenol/acetone mixtures containing 20 to 60% by weight of acetone have solidification points between +17° C. and −20° C.; in the case of phenol/acetone mixtures containing 45 to 55% by weight of acetone, the solidification points are between +5° C. and −10° C.

By adding acetone to phenol, mixtures may be established by this means at any time whose solidification point is so low that the mixture is always liquid under normal transport and storage conditions. As a result, complex treatable and/or thermally insulated transport and storage systems become unnecessary. This leads not only to considerable cost savings, but additionally considerably increases the flexibility in logistics, since no special tanks are necessary. Since the storage and transport of phenol in the liquid phase can be performed as described by the method according to the invention at ambient temperature and thus at considerably lower temperatures than hitherto, the tendency of the phenol to discolor owing to oxidation by atmospheric oxygen also decreases.

During the transport of pure liquid phenol, in addition, there is always the risk of freezing due to, for example, failure of the auxiliary heating or damage to the thermal insulation, for which reason relatively long transport distances are avoided. When phenol which has solidified is thawed out again, moreover, quality deterioration due to discoloration very frequently occurs. These defects are reliably avoided by using the method according to the invention for the phenol transport.

The conventional ambient temperatures for the transport or storage of phenol are roughly between −20° C. and +35° C., so that phenol/acetone mixtures having an acetone content up to 70% by weight are sufficient to keep the product in liquid state at all times. This not only simplifies the storage of phenol in, for example, tanks or the transport in tank trucks, tank cars, tanker ships etc., but in addition, the transport in pipelines over relatively large distances is also facilitated and sometimes even made possible for the first time. Transporting phenol by pipeline over relatively long routes has frequently failed in the past owing to the fact that it was not economically efficient on account of the necessity for heated and insulated piping. In the case of pipes laid below ground, in addition, water must be kept away from the insulation, or an expensive water-impermeable insulation must be chosen.

In the case of transport of phenol/acetone mixtures by pipeline, the insulation can be omitted completely. By changing the acetone content, moreover, the solidification point of the mixture can be adapted to the external conditions for a short time. For interruptions in the transport operation, a more acetone-rich mixture can also be introduced into a pipe, which covers all extreme external conditions.

Later removal of the acetone to produce pure phenol can be omitted for those phenol applications in which phenol and acetone are in any case used together, for example in the further processing of phenol to bisphenol A, which is of importance economically and by volume. The transhipment and transport of a phenol/acetone mixture lends itself perfectly to just this type of application. In this case also great advantages in terms of costs and flexibility are achieved; and, as explained above, the acetone added need not be removed for the further processing.

The tank storage capacity at the receiver/further processor can be designed to be correspondingly smaller. This decreases the capital costs and the current assets of bisphenol A plants.

Just-in-time delivery agreements are also simpler to organize, in particular if the distance between supplier and customer enables the use of a pipeline connection. The transport of a mixture of phenol and acetone offers advantages not only when both substances are in any case required in the following production operation.

The mixture of substances can be stocked in distribution centers which are easily accessible to the customer by means of this invention. Acetone can be released from the mixture at any time as required as a pure substance by simple distillation. Likewise, pure phenol can be re-isolated as required by distilling off the acetone. Thus, it is possible to have both pure substances available at any time within easy reach of the customer, and at the same time to utilize the additional advantages of transport and storage of the mixture of substances.

If the phenol is prepared by the Hock process, acetone is produced as coupling product and is thus generally available in a sufficient amount for the employment of the method according to the invention. Employing the method according to the invention is therefore particularly simple and advantageous if the phenol is produced by the Hock process.

Having generally described this invention, a further understanding can be obtained by reference to certain specific examples which are provided herein for the purpose of illustration only and are not intended to be limiting unless otherwise specified. Further, the following Examples are also described in priority document German patent application 196 40 710,9 filed Oct. 2, 1996, which is incorporated herein by reference.

EXAMPLES

Example 1

Transport of Phenol by Road and Rail in Central Europe in Summer

If the phenol is diluted with acetone until the mixture contains 40% by weight of acetone, a solidification point of 8° C. is produced. This mixture is not at risk of freezing in the summer months in central Europe. The transhipment facilities themselves as well as the transport containers do not need to be heated or insulated. This not only results in cost savings, but additionally increases the flexibility in logistics.

Example 2

Transport of Phenol by Road and Rail in Eastern Europe in Winter

In eastern Europe, temperatures of −20° C. are normally expected in winter. A mixture containing 60% by weight of acetone does not solidify until −20° C. In particular, because of the long transport routes, eliminating the risk of freezing offers great advantages. When phenol which has solidified is thawed out again, moreover, quality deterioration due to discoloration very frequently occurs. This problem is avoided when the method according to the invention is used.

Example 3

Tank Storage in Central Europe

If pure phenol is stored in tanks, the tanks must be insulated and heated. In an appropriate mixture with acetone, uninsulated tanks can be used, which not only reduces the costs, but simultaneously also ensures flexibility in tank usage. An amount of 55% by weight of acetone in the mixture decreases the solidification point to as low as −11° C.

Example 4

Transport by Ship

If pure phenol is transported by ship, insulation from the surrounding water is particularly important, since the cooling action of water is considerably greater than that of air. Shipments in uninsulated ship's tanks are simpler to organize and, in addition, cheaper than shipments in insulated and treatable ship's tanks. In order to achieve a solidification point below 0° C., a mixture containing 50% by weight of acetone must be established.

Example 5

Underground Pipeline Transport Over 5 km

In an actual case, a continuous transport by pipeline of pure phenol over 5 km in Belgium was studied in comparison with an alternative transport by ship. The transport of pure phenol by pipeline proved to be uneconomic. However, if instead a phenol/acetone mixture containing at least 45% by weight of acetone is transported, laying an uninsulated underground pipe is sufficient. Continuous transport by pipeline becomes more economical by this means than transport by ship. The calculated payback time is less than 2 years.

Example 6

Overground Transport by Pipeline Over 2 km

For a project in the southern USA, transport by pipeline from the ship's landing stage to the tank storage facility 1.5 km away was investigated. The pipe is intended to be used for unloading and loading ships. The construction costs for a heated and insulated DN 200 pipe are approximately 50% higher than for an uninsulated pipe for an acetone/phenol mixture, with a second pipe for acetone not yet having been included in the calculation.

Example 7

Transport by Pipeline Over 20 km

Transport of pure phenol by pipeline in a heated and insulated pipe is considerably more expensive than an alternative transport using vehicles or ships. In addition, only with considerable expenditure could the faultless functioning of the heating and insulation of the pipeline be ensured. Therefore, a project of this type also fails due to technical problems.

In this actual case, as an alternative, an uninsulated DN 80 pipe was used as the basis for the phenol transport according to the invention, which pipe is laid on an existing substructure. If 50,000 metric tons per year of a mixture of phenol containing 55% by weight of acetone are transported, the mixture remains liquid down to −10° C. The transport cost advantage in comparison to land vehicles gives a payback time of considerably less than 2 years.

Example 8

Recovery of Phenol and Acetone From the Transport/Storage Mixture

Phenol and acetone are very easy to separate by distillation. In a continuous distillation column, pure acetone can be produced as top product and pure phenol as bottom product. In a distillation column operated batchwise, pure acetone can be distilled off as the first fraction. The second fraction contains a mixture which can be recycled to the feed tank. Pure phenol remains as bottom product.

Combined storage and separation plants of this type can be used anywhere in regional markets.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method which comprises transporting a nonreactive liquid mixture of (1) an amount greater than 0 and up to 70% by weight of acetone and (2) phenol.

2. The method as claimed in claim 1, wherein the mixture comprises 20 to 60% by weight of acetone.

3. The method as claimed in claim 2, wherein the mixture comprises 45 to 55% by weight of acetone.

4. The method as claimed in claim 1, wherein said transporting is in a vessel free from a protective treatment, thermal insulation or heating.

5. The method as claimed in claim 1, wherein the phenol is prepared by the Hock process.

6. The method of claim 1, further comprising, after transporting, condensing said liquid mixture in the presence of an acid to form bisphenol A.

7. The method of claim 1, wherein said phenol remains liquid at a temperature above −40° C.

8. The method of claim 2, wherein said phenol remains liquid at a temperature above 20° C.

9. The method of claim 3, wherein said phenol remains liquid at a temperature above 0° C.

10. The method of claim 1, wherein the nonreactive liquid mixture consists of acetone and phenol.

11. A storage and/or transport vessel comprising a nonreactive liquid mixture of (1) an amount greater than 0 and up to 70% by weight of acetone, and (2) phenol, wherein said vessel is free from a protective treatment, thermal insulation or heating.

* * * * *